(12) United States Patent
Michalak

(10) Patent No.: US 8,991,399 B2
(45) Date of Patent: Mar. 31, 2015

(54) SLEEP APNEA PREVENTION MASK

(71) Applicant: Andre Michalak, Arlington, VA (US)

(72) Inventor: Andre Michalak, Arlington, VA (US)

(*) Notice: Subject to any disclaimer, the term of this patent is extended or adjusted under 35 U.S.C. 154(b) by 0 days.

(21) Appl. No.: 13/957,568

(22) Filed: Aug. 2, 2013

(65) Prior Publication Data

US 2015/0034092 A1 Feb. 5, 2015

(51) Int. Cl.
*A61F 5/56* (2006.01)
*A41D 13/11* (2006.01)

(52) U.S. Cl.
CPC .............. *A41D 13/1169* (2013.01); *A61F 5/56* (2013.01); *Y10S 602/902* (2013.01)
USPC .......................................... 128/848; 602/902

(58) Field of Classification Search
CPC ........................................................ A61F 5/56
USPC ................. 128/846, 848, 859–860, 857, 868, 128/897–898, 207.15; 602/902
See application file for complete search history.

(56) References Cited

U.S. PATENT DOCUMENTS

| | | | | |
|---|---|---|---|---|
| 2,922,418 A | * | 1/1960 | Heffernan et al. | 128/206.15 |
| 4,711,237 A | * | 12/1987 | Kaiser | 128/859 |
| 6,076,526 A | * | 6/2000 | Abdelmessih | 128/848 |
| 6,089,232 A | * | 7/2000 | Portnoy et al. | 128/848 |
| 6,494,209 B2 | | 12/2002 | Kulick | |
| 7,451,766 B2 | | 11/2008 | Miller | |
| 2008/0041397 A1 | * | 2/2008 | Hirs | 128/848 |

* cited by examiner

*Primary Examiner* — Alireza Nia
*Assistant Examiner* — Tarla Patel
(74) *Attorney, Agent, or Firm* — Michael L. Greenberg, Esq.; Greenberg & Lieberman, LLC

(57) ABSTRACT

A sleep apnea prevention sleep-aid mask is described. The sleep-aid mask is configured to secure the lips of a user together in a natural state, in order to encourage the respiratory system of the user to employ the nasal passages rather than the mouth for respiration. A pad equipped with a perforated mesh or channel is positioned over the lips and mouth of the user, and secured in position on the user via an adhesive, which temporarily affixes the pad to the face of the user. The sleep-aid mask is preferably shaped and sized according to the specific size of the user's face, and is configured to limit the effective diameter of the mouth of the user, in order to cause continued use of respiration via the nasal passages.

19 Claims, 4 Drawing Sheets

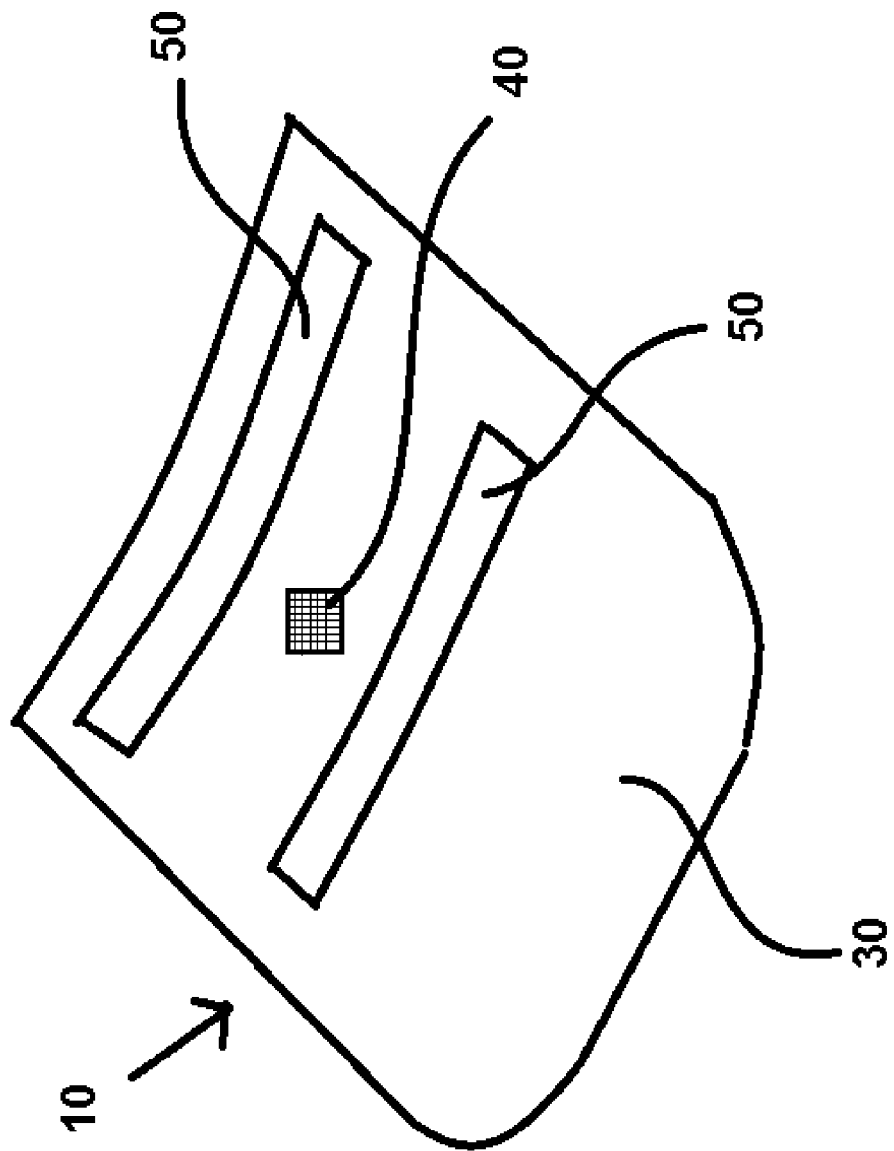

SLEEP APNEA PREVENTION MASK

FIELD OF THE PRESENT INVENTION

The present invention relates to face masks designed to be worn by people during sleep, and more specifically, to sleep masks configured to cover the mouth and lips of the user. The present invention is oriented toward reinforcing healthy breathing patterns, specifically breathing patterns that do not induce sleep apneas, as well as encouraging the act of breathing through the nasal passages.

BACKGROUND OF THE PRESENT INVENTION

Occasionally, it is known that some individuals suffer from mild to severe sleep disorders. Some individuals merely have difficulty falling asleep, or perhaps staying asleep, while others have difficulties maintaining consistent, healthy breathing patterns. Individuals that suffer from sleep apnea are known to have pauses or gaps in breathing that can last 20 seconds or more, and in some cases, the apnea can last for minutes. This can cause a variety of problems for the individual, ranging from drowsiness, irritability, difficulty storing memories, incomplete sleep cycles, slower reaction time, daytime fatigue, and even impaired vision.

Additionally, it is known that sleep apnea can be difficult to initially detect, and can also be difficult to effectively treat. Frequently individuals suffering from sleep apnea are unaware of experiencing apneas throughout the night, and are unaware of what is causing their drowsiness the next day. Once a formal sleep study is conducted, diagnosis of sleep apnea can be made.

Treatments after diagnosis often include lifestyle changes, medication, and behavioral therapy. Additionally, in some cases a CPAP (Continuous Positive Air Pressure) device can be used and a splint employed in order to facilitate and encourage healthier breathing and breathing patterns during sleep. However, many of these treatments could be aided, and in some cases, be rendered unneeded via an external device that could potentially eliminate the need for surgery, and augment the efficacy of medication and lifestyle changes to the overall treatment for sleep apnea. Such a device would preferably orient the lips and jaw of the individual in order to facilitate ideal respiratory resting posture, and encourage the individual to inhale and exhale through the nasal passages, aiding in the prevention of sleep apneas.

Thus, there is a need for a device capable of externally maintaining the lips and jaw of the face of a user in a relaxed, closed posture, in order to facilitate respiration through the nasal passages and aide in the treatment and prevention of sleep apnea.

U.S. Pat. No. 6,494,209B2 filed by George Kulick on Dec. 17, 2002 is for a mouthpiece and tubing. Kulick is similar to the present invention in that it attempts to solve sleep disorders. However, Kulick employs a mouthpiece engineer to fit within and around the mouth of the user, whereas the present invention is designed to remain wholly external to the mouth of the user.

U.S. Pat. No. 7,451,766B2 filed on Nov. 18, 2008 by Chipp Miller is for an enhanced breathing device titled "tubing based device for snoring and/or sleep apnea." Miller addresses the problem of sleep apnea as well, but employs additional tubing to direct respiration, unlike the present invention, which preferably uses a pad and integrated mesh perforation to direct air flow.

SUMMARY OF THE PRESENT INVENTION

The present invention is a sleep-aid device designed to hold a user's mouth in a natural closed position, helping to ensure that the tongue and jaw of the use will not relax during sleep and cause pauses in breathing known as apneas. The present invention employs a form of hypoallergenic adhesive affixed to a paper-thin, perforated silicone or cloth pad, similar in construction to 3M™ Medipore™ in order to securely and temporarily affix the present invention to the face, namely the cheeks, lips, and/or jaw of the user. The sleep aid of the present invention is designed to hold the lips of the user closed, encouraging breathing through the nasal passages and nostrils.

A permeation, consisting of a thin mesh or cylindrical channel is disposed just above or between the adhesive of the present invention, and is positioned such that the permeation lies over or just above the mouth of the user during use. The permeation exists to provide an alternate channel for respiration through the mouth in the event that the nasal passage of the user becomes blocked, forcing the user to breath through his or her mouth.

The pad of the present invention is preferably configured to conform to the shape of the user's face, and provide a semi-secure seal over the mouth of the user during use. While the seal need not be completely air-tight, any restriction over the mouth of a user during sleep will help to curtail his or her use of the mouth to breathe.

When the present invention is properly positioned and affixed to the face of the user, the user's respiration is channeled, and therefore encouraged to flow through the nasal passages of the user rather than through the mouth. Through this method of respiration, it is less likely for the user to suffer from a sleep apnea.

BRIEF DESCRIPTION OF THE DRAWINGS

FIG. 4 depicts an alternate embodiment of the present invention, highlighting an alternate placement of the adhesive of the present invention.

DETAILED DESCRIPTION OF THE PREFERRED EMBODIMENT

Figure 1:
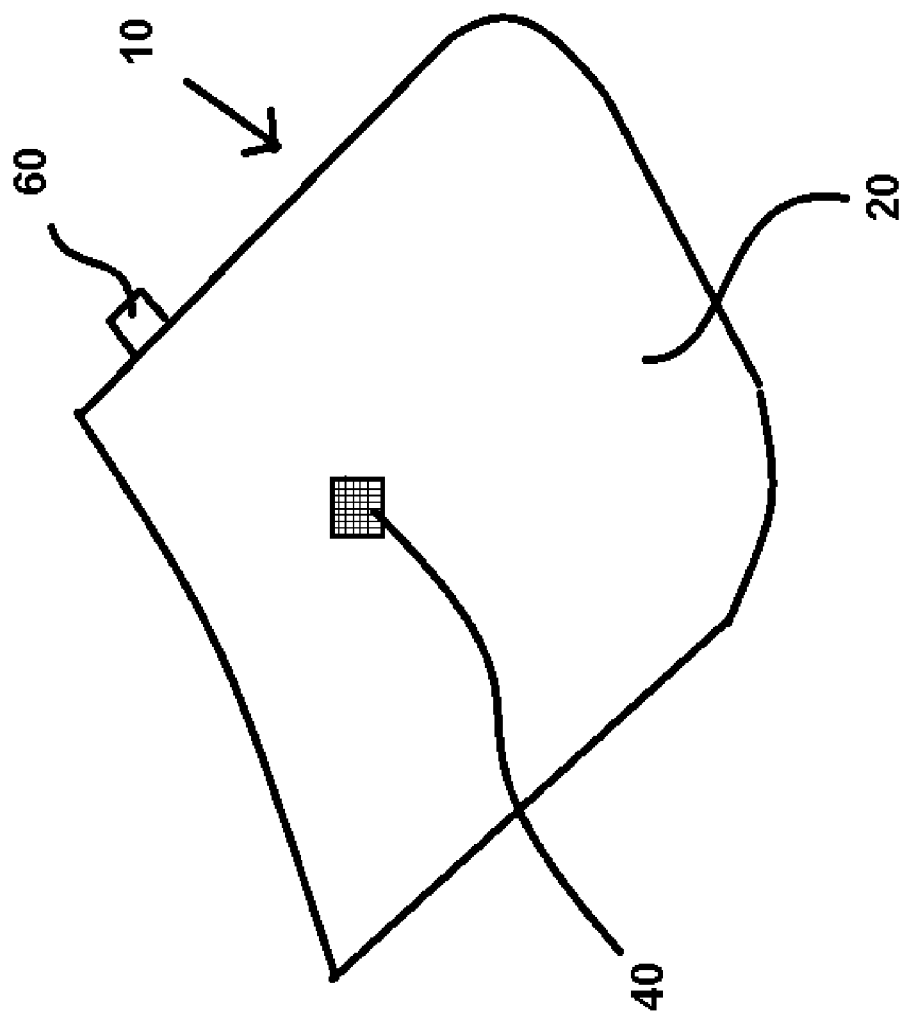
FIG. 1 depicts the present invention as viewed from the front.
Figure 2:
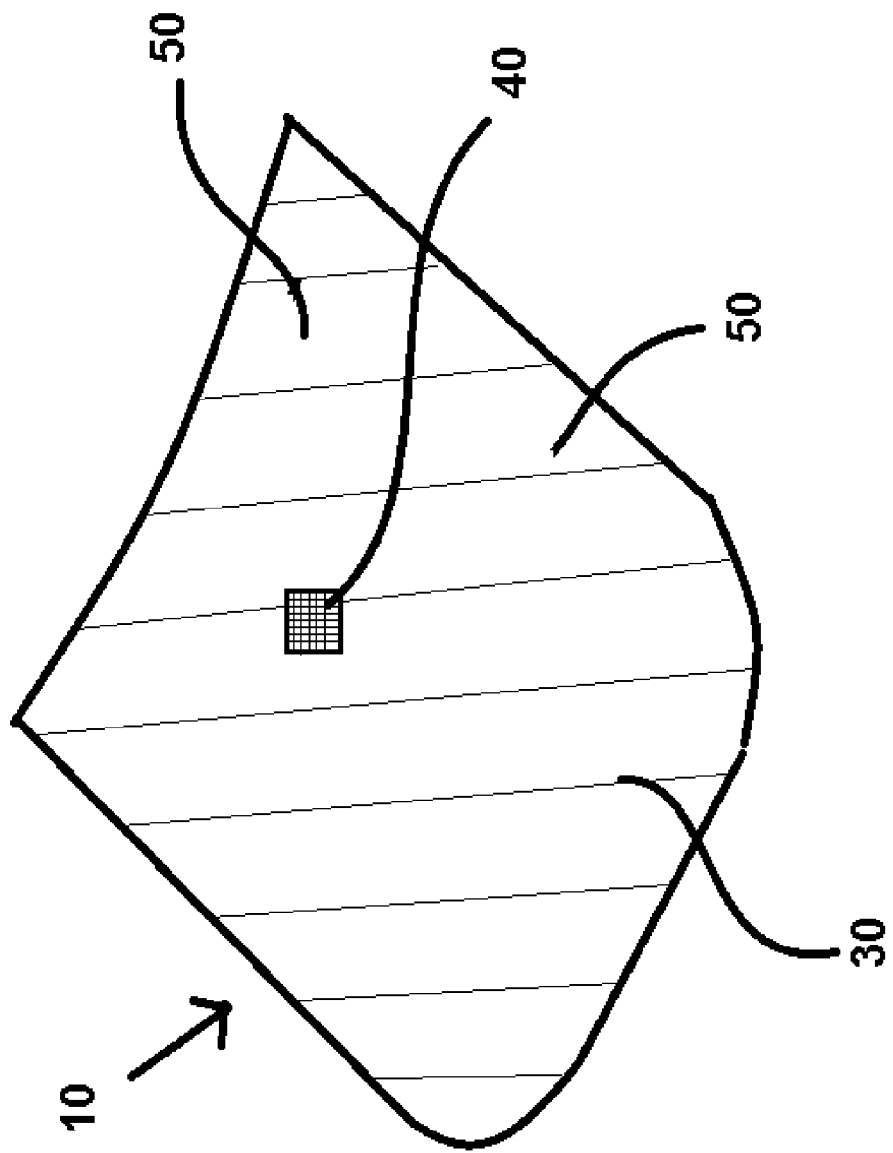
FIG. 2 shows the present invention as viewed from the back.
Figure 3:
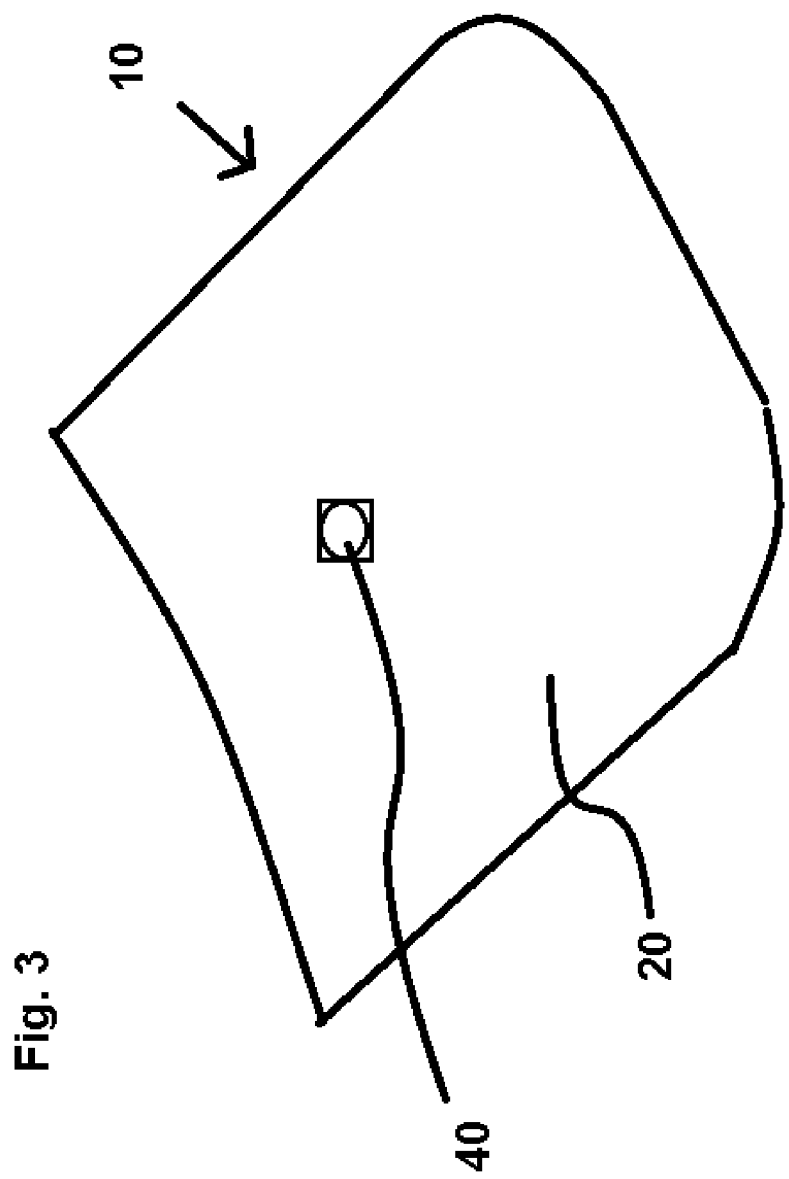
FIG. 3 exhibits an alternate embodiment of the present invention, exhibiting a cylinder.

The present invention is a sleep mask configured to be worn on the face of a user during sleep. The present invention preferably consists of a pad (10) that is preferably a paper-thin cloth, a silicone sheet, a woven paper, or similarly soft material. Due the preferably soft and flexible construction of the pad (10), it is envisioned that the preferred embodiment of the pad (10) is stretchable, yet strong enough not to break or puncture when stretched. The pad (10) has a front side (20) and a back side (30). At the center of the pad (10), a permeation (40) exists to provide a restricted channel for air to pass through. The permeation (40) is preferably small, no larger than a half inch in diameter, and may be embodied by a small hollow cylinder as seen in FIG. 3. However, the permeation (40) employed by the preferred embodiment of the present invention is a mesh, gas-permeable fabric, as seen in FIG. 1 and FIG. 2, in order to provide the constricted, alternate passage for air in the event that the user's nasal passage becomes clogged, and alternate breathing through the mouth is required.

The back side (30) of the pad (10) is equipped with an adhesive (50) which is strong and water-resistant enough to bind the pad (10) temporarily to skin, yet preferably do not irritate the skin or leave a sticky residue on the skin. The adhesive (50) can be seen in FIG. 2, and is represented by diagonal, thin lines across the back side (30) of the pad (10). The adhesive (50) is preferably clear in the preferred embodiment of the present invention, however it can be envisioned that it may have a slight coloration to it, in order to help the user easily differentiate between the back side (30) and the front side (20) of the pad (10). The adhesive (50) is preferably capable of remaining in position even in the event that the user begins to sweat. Additionally, the adhesive (50) of the present invention is preferably non-toxic. The non-toxicity of the adhesive (50) is critical as the adhesive (50) is preferably positioned such that it comes into close contact with the lips and/or mouth of the user. The adhesive (50) of the present invention is intended to affix the present invention to the upper lip and lower lip and jaw of the user. The adhesive (50) of the present invention is preferably oriented just above and below the permeation (40).

Some embodiments of the present invention are preferably equipped with a release tab (60). The release tab (60) is preferably positioned on the left or right side of the pad (10), and is free from adhesive. The release tab (60) is designed to facilitate the removal of the present invention from the face of a user after the sleep session is completed. To use the release tab (60), the user simply pulls the release tab (60) out and away from the user's face, providing for the pad (10) to be peeled off the face of the user quickly and easily.

In some embodiments of the present invention, the adhesive (50) covers the entirety of the back side (30) of the pad (10) of the present invention. The adhesive (50) of the present invention is preferably covered with an adhesive backing, such as a piece of waxed paper, in order to keep the adhesive (50) clean and sterile until time of use. Similarly, in some embodiments of the present invention, such as those sized for smaller mouths or faces, the adhesive (50) of the present invention may also encompass or come into contact with the permeation (40) or come very near to the site of the permeation (40) of the present invention. The adhesive (50) is also crafted to leave little to no sticky residue behind, and is capable of holding a stable position on the face of the user that endures for the duration of the sleep session.

It is envisioned that the present invention is capable of remaining securely affixed to or over the lips and jaw of the user for the duration of the sleep session due to the strength and rigidity of the paper-thin and/or paper-like cloth or silicone used in the pad (10), as well as due to the efficacy of the adhesive (50) employed by the present invention. It should be noted that the adhesive (50) and pad (10) that the present invention are equipped with are preferably hypoallergenic and kept in a sterile container until use. The present invention may also be kept in a sterile, preferably paper envelope, similar to a conventional adhesive bandage, in order to ensure dirt and other contaminants do not compromise the sterility of the pad (10).

Alternate embodiments of the present invention may include variations on the size of the permeation (40). For example, for users with a large lung capacity, the standard size of the permeation (40) of the present invention may be too small, which could cause an individual to faint from a lack of oxygen if his or her nasal passages become blocked during the user of the present invention. As such, some versions of the present invention may be equipped with a permeation (40) that has a larger diameter, or if the permeation (40) is a mesh screen, the screen may be larger or equipped with additional small holes to permit slightly greater air flow.

Similarly, the pad (10) of the present invention may be available in a variety of sizes in order to accommodate all shapes and sizes of faces. While it is envisioned that a 'one-size-fits-all' size of pad (10) will likely function appropriately for most individuals, larger sizes may be needed for individuals with irregularly shaped or sized mouths or other facial features.

In the event that the user has a full face beard, the adhesive (50) of the present invention will be less effective than when placed on a user without facial hair. As such, it is envisioned that an alternate embodiment of the present invention may be equipped with at least one elastic band which may facilitate the stable placement of the pad (10) on to the user's face. It is envisioned that the elastic band would preferably be affixed to the sides of the pad (10), and be capable of retaining the pad (10) in an approximately ideal location by securing the pad (10) to the user's face via the elastic band around the user's ears or the back of his or her head. Adhesive (50) is preferably still employed in this alternate embodiment of the present invention, however it is understood that facial hair would likely infringe on the adhesive's capacity to remain affixed to the face of the user for the duration of the sleeping session.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

I claim:

1. A method for preventing sleep apnea of a user, comprising:
    maintaining an upper lip and a lower lip of a face of the user in a closed posture;
    maintaining a jaw of the face of the user in a closed posture;
    orienting adhesive just above and below a permeation in a pad;
    affixing the pad to the upper lip and the lower lip of the user with the adhesive while said maintaining the lips of the face of the user in the closed posture;
    affixing the pad to the jaw of the face of the user with the adhesive while maintaining the jaw of the face of the user in the closed posture;
    covering a mouth of the user with the pad;
    covering the upper lip and the lower lip of the user with the pad;
    covering cheeks of the user with the pad;
    the pad facilitating respiration through the nasal passages, preventing airflow through the mouth of the user;
    the pad remaining wholly external to the mouth of the user;
    the pad holding the mouth of the user in a natural closed position;
    ensuring that a tongue of the user will not relax during sleep;
    ensuring that the jaw of the user will not relax during sleep;
    forming a semi-secure seal over the mouth of the user with the pad; and
    ensuring dirt and contaminants do not compromise sterility of the pad.

2. The method of claim 1, further comprising positioning the pad so that the permeation lies over the mouth of the user.

3. The method of claim 2, further comprising:
    removing the pad via a release tab; and
    keeping the adhesive and the pad in a sterile container until use.

4. The method of claim 1, further comprising positioning the pad so that the permeation lies just above the mouth of the user.

5. The method of claim 4, further comprising:
pulling a release tab out and away from the face of the user once a sleep session has completed, and thus pulling the pad off the face of the user; and
keeping the adhesive and the pad in a paper envelope until use.

6. The method of claim 1, further comprising removing the pad via a release tab.

7. The method of claim 1, further comprising pulling a release tab out and away from the face of the user once a sleep session has completed, and thus pulling the pad off the face of the user.

8. The method of claim 1, further comprising keeping the adhesive and the pad in a sterile container until use.

9. The method of claim 1, further comprising keeping the adhesive and the pad in a paper envelope until use.

10. A method for preventing sleep apnea of a user, comprising:
orienting adhesive just above and below a permeation in a pad;
affixing the pad to an upper lip and a lower lip of the user with the adhesive;
affixing the pad to the jaw of the user with the adhesive ensuring that a tongue of the user will not relax during sleep;
covering a mouth of the user with the pad;
covering the upper lip and the lower lip of the user with the pad;
covering cheeks of the user with the pad;
the pad facilitating respiration through the nasal passages, preventing airflow through the mouth of the user;
the pad remaining wholly external to the mouth of the user;
the pad holding the mouth of the user in a natural closed position;
forming a semi-secure seal over the mouth of the user with the pad; and
ensuring dirt and contaminants do not compromise sterility of the pad.

11. The method of claim 10, further comprising positioning the pad so that the permeation lies over the mouth of the user.

12. The method of claim 11, further comprising:
removing the pad via a release tab; and
keeping the adhesive and the pad in a sterile container until use.

13. The method of claim 10, further comprising positioning the pad so that the permeation lies just above the mouth of the user.

14. The method of claim 13, further comprising:
pulling a release tab out and away from the face of the user once a sleep session has completed, and thus pulling the pad off the face of the user; and
keeping the adhesive and the pad in a paper envelope until use.

15. The method of claim 10, further comprising removing the pad via a release tab.

16. The method of claim 10, further comprising pulling a release tab out and away from the face of the user once a sleep session has completed, and thus pulling the pad off the face of the user.

17. The method of claim 10, further comprising keeping the adhesive and the pad in a sterile container until use.

18. The method of claim 10, further comprising keeping the adhesive and the pad in a paper envelope until use.

19. A method for preventing sleep apnea of a user, comprising:
maintaining the lips of a face of the user in a closed posture;
orienting adhesive just above and below a permeation in a pad;
affixing the pad to the lips of the user with the adhesive while said maintaining the lips of the face of the user in the closed posture;
covering the mouth of the user with the pad;
covering the lips of the user with the pad;
the pad facilitating respiration through the nasal passages, preventing airflow through the mouth of the user;
the pad holding the mouth of the user in a natural closed position; and
forming a semi-secure seal over the mouth of the user with the pad.

* * * * *